United States Patent [19]

Engelhart et al.

[11] 4,397,851

[45] Aug. 9, 1983

[54] 2,3-DIHALO-2,3-(DISUBSTITUTED) PROPANOATE ANTIMICROBIAL COMPOUNDS

[75] Inventors: John E. Engelhart, Westfield, N.J.; Marshall R. Angeles, Scotchplains, both of N.J.; Michael J. D'Errico, Flossmoor, Ill.

[73] Assignee: Merck & Co., Inc., Rahway, N.J.

[21] Appl. No.: 333,269

[22] Filed: Dec. 22, 1981

[51] Int. Cl.$^3$ ............... A61K 31/495; C07D 239/26; C07D 211/32; C07C 69/612; C07C 69/635

[52] U.S. Cl. ................... 424/250; 560/124; 260/465 D; 260/465.4; 424/304; 424/305; 424/308; 424/251; 424/263; 424/267; 424/270; 424/272; 424/273 P; 424/273 R; 424/275; 424/285; 544/335; 544/399; 546/248; 546/335; 548/203; 548/214; 548/236; 548/248; 548/342; 548/353; 548/367; 548/377; 548/572; 549/79; 549/499; 560/1; 560/105; 560/122

[58] Field of Search ............... 560/105, 192, 226, 122, 560/123, 124, 1; 424/304, 305, 308, 311, 313, 250, 251, 263, 267, 270, 272, 273 P, 273 R, 275, 285, 274; 260/326.2, 326.8, 347.5, 465 D, 465.4; 544/335, 399; 546/248, 335; 548/203, 214, 236, 248, 342, 353, 367, 377; 549/79

[56] References Cited

U.S. PATENT DOCUMENTS

| | | | |
|---|---|---|---|
| 2,320,034 | 5/1943 | D'Ianni ................... | 560/192 X |
| 3,317,568 | 5/1967 | Wygant et al. ............ | 560/192 X |
| 3,608,084 | 9/1971 | Matt ....................... | 260/465.7 |
| 3,833,731 | 9/1974 | Grier et al. ............... | 424/304 |
| 3,873,597 | 3/1975 | Harmetz et al. .......... | 260/465.7 |
| 3,877,922 | 4/1975 | Grier et al. ............... | 71/67 |
| 4,328,363 | 5/1982 | Heiba et al. .............. | 560/192 X |

FOREIGN PATENT DOCUMENTS

50-123828 9/1975 Japan .
1424943 2/1976 United Kingdom .

OTHER PUBLICATIONS

Gershon, et al., J. Med. Chem. 20(4), 606–609, (1977), Chem Ab. 84:39698t.
Motoyama, et al., Sankyo Kenkyusho Nempo 23:233–244, (1971), Chem. Ab. 77:30239s.

*Primary Examiner*—Natalie Trousof
*Assistant Examiner*—Vera C. Clarke
*Attorney, Agent, or Firm*—Alice O. Robertson; Raymond M. Speer

[57] ABSTRACT

Antimicrobial compounds of the formula:

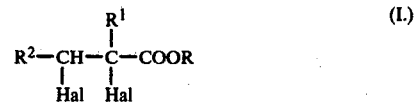

(L)

wherein
Hal is bromine or chlorine; R is $C_{1-4}$ alkyl, straight or branched chain; and one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

4 Claims, No Drawings

2,3-DIHALO-2,3-(DISUBSTITUTED) PROPANOATE ANTIMICROBIAL COMPOUNDS

BACKGROUND OF THE INVENTION

1. Field of the Invention

The present invention is concerned with novel compounds which are 2,3-dihalo-2,3-(disubstituted)-propanoates. The present invention is also concerned with antimicrobial compositions containing these novel compounds as active ingredients, as well as with a method of inhibiting the growth of bacteria, yeast, fungi, and algae by contacting said bacteria, yeast, fungi, and algae with the novel compounds of the present invention. These novel antimicrobial compounds have a number of important industrial and agricultural applications.

As used herein, the term "antimicrobial" describes the killing of, as well as the inhibition of or control of the growth of bacteria, yeasts, fungi, and algae. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber and machine industries. Important applications include: inhibiting the growth of bacteria in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; as a hard surface disinfectant to prevent growth of bacteria and fungi on walls, floors, etc.; and in swimming pools to prevent algae. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Antimicrobial compounds are also utilized for agricultural applications, for example in preventing or minimizing the growth of harmful bacterial, yeast, and/or fungi on plants, trees, fruit seeds, or soil.

A particular application for which the antimicrobial compounds of the present invention have been found especially useful is in the protection of paint films from attack by fungi. Paint film fungicides which can preserve paint films from the deleterious effects of fungal attack which occur during weathering of the paint film have long been sought. Few, however, have been found due to the stringent requirements for such a successful paint film fungicide. Moreover, the ability to provide in-can preservative activity, as well as paint film protection, is also desirable. However, this additional characteristic is seldom seen in a paint film fungicide.

2. Brief Description of the Prior Art

Matt U.S. Pat. No. 3,608,084 describes halogenated aliphatic nitriles for controlling the growth of aerobacter bacteria in industrial water systems.

Grier, et. al., U.S. Pat. Nos. 3,833,731 and 3,877,922; and Harmetz, et. al. U.S. Pat. No. 3,873,597 describe 2-bromo-2-bromomethylglutaronitrile and related compounds and their use as antibacterial, antifungal, and algicidal agents.

Gershon, et. al., in *J. Med. Chem.* 20(4), 606–9 (1977), describe the antifungal properties of 2-bromo-3-fluorosuccinic acid esters.

Rader et al, British Pat. Spec. No. 1,424,943 describes α-(halomethyl)mandelonitrile microbiocides.

Tanaka et al., Japan. Kokai No. 75,123,828 (9-29-75), *Chem. Ab.* 84:39698t, disclose ethyl 2,3-dibromopropionate as an intermediate for preparing dithiolane herbicides and fungicides.

Motoyama et al., *Sankyo Kenkyusho Nempo* 23:233–44 (1971), *Chem. Ab.* 77:30239s, disclose 2,3-dichloropropionic acid as a herbicide.

However, there is no suggestion in any of the above references of the particular compounds of the present invention or their broad spectrum of antimicrobial activity.

DETAILED DESCRIPTION OF THE INVENTION AND PREFERRED EMBODIMENTS

In accordance with the present invention there are provided novel 2,3-dihalo-2,3-(disubstituted)propanoates of the formula:

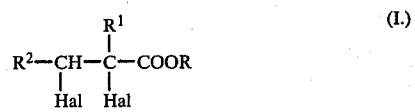

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

Particularly preferred compounds of the present invention are the following: ethyl 2,3-dibromo-3-phenylpropanoate.

In accordance with the present invention there is further provided an antimicrobial composition comprising a carrier and an antimicrobially effective amount of a compound of the formula:

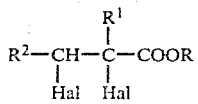

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

The 2,3-dihalo-2,3-(disubstituted)propanoate active ingredient of the antimicrobial composition of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the 2,3-dihalo-2,3-(disubstituted)propanoate is liquid, it may be employed neat or may be incorporated into various formulations, both solid and liquid, as an adsorbate on suitable inert carriers such as talc, clays, diatomaceous earth and the like.

Thus, it will be appreciated that the 2,3-dihalo-2,3-(disubstituted)propanoate may be employed to form antimicrobial formulations containing such compounds as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as loweralkanols, kerosene, benzene, toluene and other petroleum distillate fractions or mixtures thereof.

It will be understood also that the 2,3-dihalo-2,3-(disubstituted)propanoate active ingredients may be used in combination one with the other as well as with other antimicrobial materials. For example, these compounds can be combined with other fungicides and bactericides such as 2-(4′-thiazolyl)benzimidazole, sorbic acid, propionic acid, mycostatin, sodium diacetate, trichomycin, amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, sodium benzoate in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations. It is quite clear also that the 2,3-dihalo-2,3-(disubstituted)propanoates can be combined with other algicidal agents such as benzalkonium chlorides and other quaternary ammonium compounds to obtain formulations particularly suitable to special problems of algae control.

In accordance with the present invention there is still further provided a method of inhibiting the growth of at least one of: bacteria, yeast, fungi, and algae, comprising contacting said bacteria, yeast, fungi, or algae, with a bactericidally, fungicidally, or algicidally effective amount of a compound of the formula:

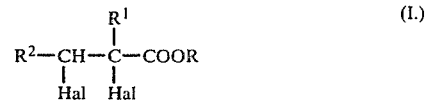

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

As noted above, the instant invention is based upon the discovery that the 2,3-dihalo-2,3-(disubstituted)-propanoates described above are effective in controlling the growth of bacteria, yeast, fungi and algae in a variety of industrial and agricultural applications. It has been found, for example, that these compounds are effective antimicrobials for the destruction or control of soil fungi and bacteria and for the protection of seeds, bulbs and plants. Also, they are effective algicides in the treatment of pools and ponds, cooling water systems and the like. The utility of the 2,3-dihalo-2,3-(disubstituted)propanoates of this invention is shown not only by their activity against bacteria and fungi responsible for stunting growth, and even destruction of many types of crop-producing plants, but also for those causing degradation and deterioration of many types of industrial products including, for example, paper, leather, textiles, aqueous systems such as adhesives, resins, drilling fluids, pigment dispersions and latex paints and oleoresinous coatings whose films are particularly vulnerable to the destructive action of fungi. The large economic losses encountered in paper-making operations caused by the accumulation of bacterial and fungal slimes in various parts of the system can be eliminated to a significant extent by use of the compounds described herein.

Thus, for pulp and paper mill systems, there is provided a method of inhibiting the growth of slime-forming bacteria, fungi, and algae, usually encountered in pulp and paper mill systems, comprising incorporating into the mass of fiber and water in such a pulp and paper mill system so as to contact said bacteria, fungi, and algae, at least a bactericidally, fungicidally, and algicidally effective amount of a compound of the formula:

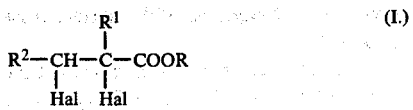

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

The antimicrobial activity of the compounds described above has been confirmed using standard laboratory techniques. They have been found effective, for example, in inhibiting bacteria including Aerobacter sp. such as *A. aerogenes*, Pseudomonas sp. such as *P. aeruginosa*. They have been found effective also against fungi including Aspergillus sp. such as *A. niger*, Pullularia sp. such as *P. pullulans*, Penicillium sp. such as *P. funiculosum*, Alternaria sp. such as *A. brassicicola*, and Saccharomyces sp. such as *S. cerevisiae*. Such bacteria and/or fungi commonly are found on cereal and grain products, on oils, on fruits and vegetables and on cosmetics, leather, electrical insulation, textiles and numerous other materials capable of supporting their growth. Also, such bacteria and/or fungi may be found on plants, seeds, fur and wood and in soils. Further, they may be used to control overgrowth of algae such as Chlorella sp. including *C. pyrenoidosa*.

As noted above, it has been found that growth of various harmful fungi and bacteria existing in soil is eliminated or limited by use of formulations containing the 2,3-dihalo-2,3-(disubstituted)propanoates described herein. The term, soil, as used here is intended to include all media capable of supporting growth of plants and may include humus, sand, manure, compost, artificially created plant growth solutions and the like.

The 2,3-dihalo-2,3-(disubstituted)propanoates described above have activity against bacteria, yeast, fungi, and algae when employed at appropriate levels of concentration and may be used to inhibit growth of these organisms. It will be obvious to those skilled in the art that the required effective concentration will vary with particular organisms and in particular applications. In general, however, effective fungicidal, bactericidal and algicidal response is obtained when the 2,3-dihalo-2,3-(disubstituted)propanoates are employed in concentrations ranging between 0.5 and 5000 ppm (parts per million).

For latex paints, latex emulsions and adhesives, amounts of from 100 to 2000 ppm of a compound of the present invention are added during manufacture of the paint, emulsion, or adhesive in order to protect the system during in-can storage against bacteria, fungi, and yeasts.

For cooling towers, amounts of from 1 to 100 ppm, and for pulp and paper mills, amounts of from 50 to 500 ppm of a compound of the present invention are added to the pulp suspension in a paper mill or to the recirculating cooling water in a cooling tower in order to inhibit the growth of slime-forming bacteria, fungi, yeasts and algae.

For metal working fluids, i.e. cutting oils, amounts of from 200 to 2000 ppm of a compound of the present invention are added to a metal working fluid concentrate in order to inhibit the growth of bacteria, fungi, and yeasts during the use cycle of an oil-water lubricant for metal surfaces.

For other applications of the type described above, amounts of from 0.005 to 0.5% by weight, based on weight of the substrate being treated, of a compound of the present invention is incorporated into, sprayed onto, used to dip, or otherwise applied to the substrate to be treated in order to prevent growth of bacteria, fungi, yeasts, and algae.

The 2,3-dihalo-2,3-(disubstituted)propanoates of the present invention may be prepared in accordance with the synthesis routes described below.

A. Compounds of Formula I where $R^1$ is hydrogen

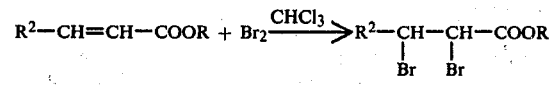

The starting materials for this route are unsaturated carboxylic acids which are readily available or which may be prepared in accordance with well-known techniques. For example, where $R^2$ is phenyl, cinnamic acid is employed. Before bromination is carried out, the acid is converted to the desired ester by well-known techniques. Also, ester starting materials are readily available in many cases.

B. Compounds of Formula I where $R^2$ is hydrogen

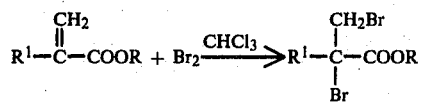

The starting materials for this route are carboxylic acids having a methylene group attached to the α-carbon. The starting materials, where $R^1$ is attached through a methylene bridge, in turn, may be prepared in accordance with a series of reactions which may be illustrated as follows:

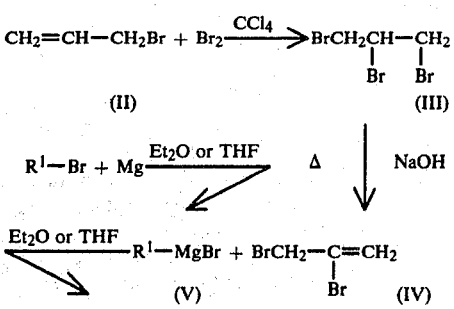

-continued

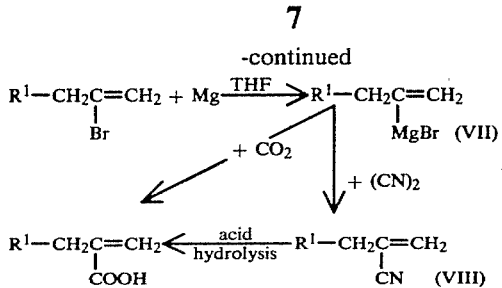

In the first two steps shown above, the intermediate 2,3-dihalo-1-propene (IV.) is prepared from the available starting material 3-halo-1-propene (II.) by halogenation, followed by selective dehydrohalogenation.

(1) The allyl bromide or chloride starting material is treated with bromine or chlorine either neat or in a chlorinated hydrocarbon solvent such as carbon tetrachloride, chloroform, or dichloromethane. The reaction is exothermic and cooling is used to maintain the reaction temperature at about room temperature. The solvent is then removed and the liquid residue is carried forward to the next step.

(2) In the second step, dehydrobromination or dehydrochlorination is carried out using a strong base such as sodium hydroxide or potassium hydroxide. Water, the salt of the base, and the product are formed in the reaction, and the reaction is carried out with vigorous boiling which results in spontaneous distillation of the product with the water, thus driving the reaction to completion.

(3) The third step involves preparation of the Grignard reagent in accordance with well known techniques.

(4) The reaction of the Grignard reagent with the propene product of the second step is exothermic, and the temperature of the reaction mixture must be kept below 15° C. in order to avoid self-coupling of the Grignard reagent and promote cross-coupling with the propene. This result can also be facilitated by the use of a catalyst such as copper (I) chloride. The solvent employed may be any inert, aprotic solvent such as diethyl ether, tetrahydrofuran, or diglyme and the like. When the reaction is complete, the solvent is removed, and the product is then separated and dissolved in a solvent for use in the next step.

(5) In the fifth step, the substituted propene from the preceding step is slowly added to magnesium turnings with vigorous stirring in order to promote solubilization of the Grignard product formed on the surface of the magnesium. The reaction is exothermic, and the reaction mixture is kept at the reflux temperature of the solvent, which is selected from the group consisting of tetrahydrofuran, diethyl ether, and diglyme. The time required for completion of the reaction depends upon the reaction temperature and upon the surface area of the magnesium, i.e., magnesium of finer mesh size will result in a faster reaction. When the reaction is complete, the reaction mixture is carried over for use in the next step without further treatment.

(6) In the sixth step cyanogenation is accomplished by reverse addition of the Grignard product of the preceding step to a saturated solution of cyanogen. It has been found that cyanogen chloride and cyanogen bromide are unacceptable reactants because they result in insignificant yields of product. Reverse addition is required in order to avoid an excess of the Grignard reactant, which can react with the product. The solvent medium in which the reaction is carried out is selected from tetrahydrofuran, diethyl ether, and diglyme. The reaction is mildly exothermic, and the reaction mixture temperature is maintained at from −20° to +20° C. in order to ensure the solubility of the cyanogen. The product is separated and carried forward to the last step.

(7) In the last step, the cyano group is converted to a carboxyl group by acid hydrolysis in accordance with well-known procedures.

Where $R^1$ is attached directly, the starting materials may be prepared in accordance with a series of reactions which may be illustrated as follows:

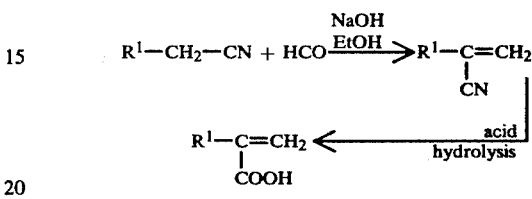

The following examples, which were actually carried out, will serve to further illustrate the present invention, without at the same time, however, constituting any limitation thereof.

EXAMPLE 1

Preparation of Ethyl 2,3-dibromo-3-phenylpropanoate

The reaction was carried out in a 250 ml 3-necked round bottomed flask equipped with a magnetic stirrer, water-cooled reflux condenser, thermometer, and bromine addition funnel. The flask was charged with ethyl cinnamate (17.6 g, 0.10 mol) and 100 ml of dry chloroform. To this solution there was added 16.0 g (0.10 mol) of bromine over a 3 hr period, and the reaction mixture was allowed to stir for an additional 20 hrs. After removing the solvent, 33.5 g (99% of theory) of a crystalline product was obtained, m.p. 70°–72° C. $^1$H NMR (CDCl$_3$, (CH$_3$)$_4$Si), δ 7.0 (s, 5H), δ 5.0–5.2 (d, J=12 Hz, 1H); δ 4.5–4.7 (d, J=12 Hz, 1H); δ 3.8–4.2 (q, J=7 Hz, 2H); δ 0.9–1.2 (t, 3H).

Elemental Analysis: Calculated for $C_{11}H_{12}O_2Br_2$: Calc'd: C, 39.32%; H, 3.60%; Br, 47.56%; Found: C, 40.16%; H, 3.62%; Br, 47.58%.

EXAMPLE 2

In order to determine antimicrobial spectrum, the following techniques are employed:

Antibacterial Activity—A stock solution of the sample to be tested is prepared in 25% methanol. Dilutions of the stock solution are made into Tryptone Glucose Extract Agar (Difco) and the agar is poured into sterile petri dishes. After hardening, the plates are streaked with an aqueous suspension of the test organism. The inoculated plates are incubated at 35°–37° C. and examined after twenty-four hours for the presence or absence of growth. The lowest concentration at which no growth occurred is reported as the "Inhibiting Concentration".

Antifungal Activity—A stock solution of the sample to be tested is prepared in 25% methanol. Dilutions of the stock solution are made into Sabouraud Maltose Agar (Difco) and the agar is poured into sterile petri dishes. After hardening, the plates are streaked with an aqueous spore suspension of the test organism. No wetting agent is used in preparation of the suspension. The inoculated plates are incubated at 28°–30° C. and examined after seven days for the presence or absence of growth. The lowest concentration at which no growth occurred, is reported as the "Inhibiting Concentration."

Employing the techniques described above, various of the 1,2-dibromo-2-cyano-2-(aryl)ethanes(propanes) of the present invention were tested at 10, 50, 100, 200, 400, 750, and 1000 ppm against the organisms, and with the results, indicated in the following table:

TABLE I

| Exp. No. | R | R¹ | R² | Aerobacter aerogenes | Pseudomonas aeruginosa | Aspergillus niger | Saccharomyces cerevisiae | Pullularia pullulans | Penicillium funiculosum | Alternaria brassicicola |
|---|---|---|---|---|---|---|---|---|---|---|
| 2 | Et | H | 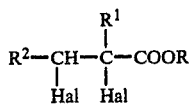 | >1000 | >1000 | 10 | 10 | 100 | 200 | 50 |

What is claimed is:

1. A compound of the formula:

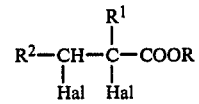 (I.)

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

2. An antimicrobial composition comprising a carrier and an antimicrobially effective amount of a compound of the formula:

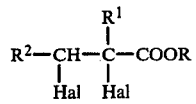 (I.)

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

3. A method of inhibiting the growth of at least one of: bacteria, fungi, and algae, comprising contacting said bacteria, fungi, or algae, with a bactericidally, fungicidally, or algicidally effective amount of a compound of the formula:

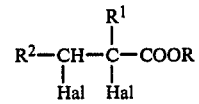 (I.)

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl; mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

4. A method of inhibiting the growth of slime-forming bacteria, fungi, and algae usually encountered in pulp and paper mill systems, comprising incorporating into the mass of fiber and water in such a pulp and paper mill system so as to contact said bacteria, fungi, and algae, at least a bactericidally, fungicidally, and algicidally effective amount of a compound of the formula:

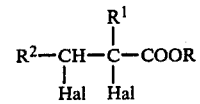 (I.)

wherein
Hal is bromine or chlorine;
R is $C_{1-4}$ alkyl, straight or branched chain; and
one of $R^1$ and $R^2$ is hydrogen and the other is selected from the group consisting of $C_{3-8}$ cycloalkyl; $C_{3-8}$ cycloalkyl $C_{1-3}$ alkyl; phenyl; phenyl $C_{1-3}$ alkyl;

mono- or disubstituted phenyl or phenyl $C_{1-3}$ alkyl wherein the substituents are halo, $C_{1-4}$ alkyl, $C_{1-4}$ alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl.

* * * * *